United States Patent [19]

Peters et al.

[11] 3,997,568

[45] Dec. 14, 1976

[54] CONVERSION OF (10'S)-ZEARALENONE TO (10'R)-ZEARALANONE

[75] Inventors: Charles Allan Peters, Terre Haute, Ind.; Richard Nelson Hurd, Wilmette, Ill.

[73] Assignee: Commercial Solvents Corporation, Terre Haute, Ind.

[22] Filed: Mar. 18, 1974

[21] Appl. No.: 452,260

[52] U.S. Cl. .................... 260/343.2 F; 260/340.9
[51] Int. Cl.$^2$ ............. C07D 313/00; C07D 317/24
[58] Field of Search ........................... 260/343.2 F

[56] References Cited

UNITED STATES PATENTS 3,852,307  12/1974  Urry ............................... 260/343.2

Primary Examiner—Anton H. Sutto
Attorney, Agent, or Firm—Morton, Bernard, Brown, Roberts & Sutherland

[57] ABSTRACT

(10'R)-Zearalanone is prepared from (10'S)-zearalenone by opening the lactone ring of the zearalenone in an alkaline medium to provide a hydroxy acid, esterifying the hydroxy acid to provide a hydroxy ester, tosylating the hydroxy ester, reacting the tosyl ester with a tetraalkyl ammonium alkyl ester to invert the (S) structure to the (R) structure, and reforming and hydrogenating the lactone to provide (10'R)-zearalanone. (10'R)-zearalanone, when present in admixture with (10'S)-zearalanone, enhances the uterotropic activity of the latter compound.

10 Claims, No Drawings

CONVERSION OF (10'S)-ZEARALENONE TO (10'R)-ZEARALANONE

This invention relates to a method of converting (10'S)-zearalenone to (10'R)-zearalanone. (10'S)-Zearalenone is the zearalenone which can be obtained, for example, from cultivating, on a suitable nutrient medium, the organism *Gibberella zeae* (Gordon), on deposit at the Northern Utilization Research and Development Division of the United States Department of Agriculture under the number NRRL-2830. By this invention, a method is provided for converting (10'S)-zearalenone to (10'R)-zearalanone by opening the lactone linkage, inverting the (S) structure to the (R) structure, and reclosing the lactone linkage.

The inversion can be conducted without racemization of the (S) and (R) structures. Upon reforming the lactone linkage, (10'R)-zearalanone is formed. (10'R)-Zearalanone, when present in admixture with (10'S)-zearalanone, enhances the uterotropic activity of the latter compound. (10'S)-Zearalanone is described in U.S. Pat. No. 3,239,354 to Hodge et al.

An alternative naming procedure to that employed herein would designate (10'S)-zearalenone as being (−)-zearalenone (see U.S. Pat. No. 3,551,455 to Giratra et al.)

(10'S)-Zearalenone may be represented by the structure

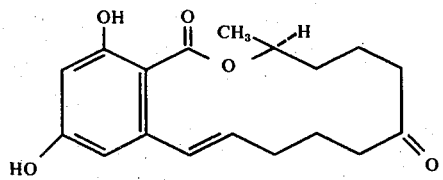

In accordance with the present invention, the phenolic hydroxy groups as well as the carbonyl function of the sixth carbon atom of the lactone ring (the 6' position) are protected during the course of the reaction. Conveniently, the phenolic hydroxy groups are converted to aralkyl ether substituents, and the 6' carbonyl function is converted to an alkyl dioxide (ketal) function. The lactone ring is cleaved in an alkaline medium to provide a hydroxy acid. To protect the carboxyl group, the hydroxy acid is converted to a hydroxy ester. Diazomethane, for instance, has been found to be a suitable esterification agent to provide the methyl ester. The methyl hydroxy ester can be tosylated with para-toluenesulfonyl chloride. Other lower paraalkylbenzene sulfonic acid anhydrides or chlorides may be useful as well. The inversion of the structure from (S) to (R) is effected by reacting the tosylated ester, or equivalent ester, with a tetraalkyl ammonium carboxylic ester to provide a (R)-carboxylic ester. This compound is then hydrolyzed in a strong alkaline medim, and the ketal group is hydrolyzed with a perchloric acid catalyst. The hydrolyzed compound is lactonized, or cyclized, using trifluoroacetic anhydride. Hydrogenation yields (10'R)zearalanone having the structure

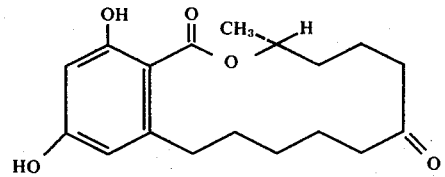

(10'R)-Zearalanone produced by the process of the present invention is substantially free of (10'S)-zearalanone and may exhibit an optical rotation at 25° C. using sodium light of about +36.8°.

In further detail, (10'S)-zearalenone, either in its 1'-trans isomer form (described in U.S. Pat. No. 3,196,019 to Andrews et al.) or in its 1'-cis isomer form (described in U.S. Patent Application No. 317,117 of Peters et al., filed Dec. 21, 1972, now abandoned) or as a mixture of 1'-trans and 1'-cis isomers (described in U.S. Pat. No. 3,624,144 to Wendler et al.), is converted to (10'R)-zeralanone, in the following manner. The phenolic functions of (10'S)-zearalenone are protected during the course of the inversion reaction by converting the hydroxy groups to ether functions. The etherification reaction is conveniently conducted in a slightly alkaline, organic solvent medium with an etherifying agent (e.g. an alkyl halide or aralkyl halide) of, say, 2 – 12 carbon atoms. The etherifying groups may be cyclic, i.e., cycloalkyl, aryl, or heterocyclic of say, 5 to 12 ring members, or acyclic, such as lower alkoxyalkyl. Included are, for instance, benzyl, bromobenzyl, and methoxymethyl substituents.

The solvent medium may often comprise an aprotic solvent, for instance, dimethylformamide, diethylene glycol dimethyl ether, methyl ethyl ketone, dimethylsulfoxide, pyridine, and the like. High boiling alcohols, e.g., butanol, may also be employed as the solvent medium. Often the alkyl halide or aralkyl halide is used in an amount in excess of that stoichiometrically required for complete reaction. Alkaline conditions may be achieved by, for example, the addition of anhydrous potassium carbonate to the mixture, and the pH of the reaction medium is preferably about 9 or 10 to 12. The reaction time and temperature will depend upon the nature of the etherifying agent and solvent medium, and the reaction will generally proceed at moderate temperatures, for example about 50° to 120° C. The structure of the ether may be illustrated as

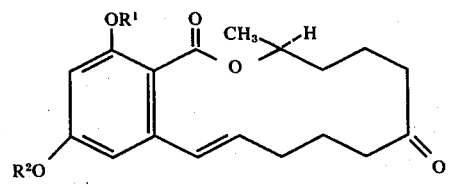

wherein $R^1$ and $R^2$ are carbon-containing substituents as described above, preferably benzyl.

The 6' keto function of the zearalenone structure needs also to be protected during the course of the inversion reaction to prevent racemization. This is conveniently accomplished by the ketalization of the carbonyl function with a diol of the formula

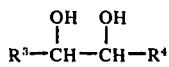

wherein R³ and R⁴ are hydrogen or lower alkyl. Ketalization of the carbonyl function may be effected prior or subsequent to the condensation reaction to protect the phenolic functions of zearalenone. Preferably, ethylene glycol is employed for the ketalization. The diol is normally present in at least a stoichiometric amount, generally in substantial excess of the amount required for complete conversion to the ketal, e.g., at least about 1.5 times the amount stoichiometrically required for complete reaction. Paratoluene sulfonic acid may be employed as a catalyst and is present in a catalytically effective amount, e.g., about 0.1 to 5 percent by weight of the zearalenone. Other catalysts for ketalization include Dowex 50 resin, a sulfonic cation exchange resin. Hydrocarbon solvent reaction medium is normally employed, such as benzene or toluene. Desirably, the hydrocarbon solvent will azeotrope with water to facilitate removal of water generated by the reaction. The reaction is often conducted under slow distillation to remove the water which is formed. The ketalized lactone may be represented by the structural formula

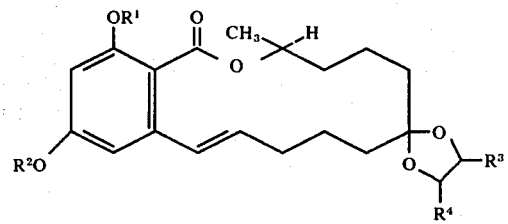

wherein R¹, R², R³ and R⁴ are as defined above.

With the carbonyl group protected, the lactone ring can be cleaved under strongly basic hydrolysis conditions. Typical conditions for the lactone ring opening include the presence of about 0.5 to 3 parts by weight of alkali metal hydroxide, e.g., potassium or sodium hydroxide, per part of lactone; a strong aprotic solvent such as dimethyl sulfoxide, dimthyl formamide, diethylene glycol dimethyl ether, and the like; and an essentially inert atmosphere, conveniently nitrogen, at temperatures in the range of about 90° to 140° C., preferably about 100° to 130° C. Upon completion of the ring opening reaction, the reaction mixture may be acidified with an inorganic acid, e.g., sulfuric acid. The cleaved structure may be represented as

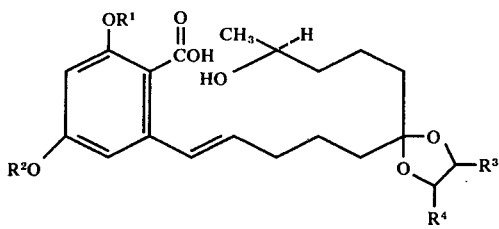

wherein R¹, R², R³ and R⁴ are defined as above.

Following the ring opening reaction, the carboxylic function should be protected during tosylation of the hydroxyl group at the 10' position by, for instance, esterification, for example to provide a lower alkyl ester. Conveniently, the esterification is conducted by reacting diazomethane with the hydroxy acid to provide the methyl hydroxy ester thereof. Diazomethane, because of its relatively high explosive and toxicity risk, may advantageously be freshly procured by the addition of potassium hydroxide to N-methyl nitrosourea. Generally, the diazomethane is used in an amount in excess of the stoichiometric amount required for complete reaction, and subsequent to conducting the tosylation reaction, acetic acid or other organic acid is employed to decompose the excess reagent. The esterification reaction may be conducted at ambient conditions, e.g., about 10° to 35° C., and provides a hydroxy ester which may be represented by the structure

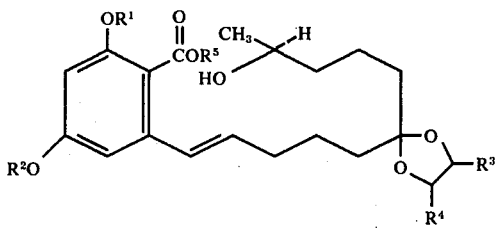

wherein R¹, R², R³ and R⁴ are as defined above and R⁵ is lower alkyl, preferably methyl.

The inversion of the (S) structure to the (R) structure is effected by converting the tosylate, mesylate, brosylate or equivalent ester, of the above-described hydroxy ester to a corresponding, but inverted, carboxylic ester. First, the sulfonic acid ester can be prepared by reacting the hydroxy ester with an excess of the amount stoichiometrically required for complete reaction of phenylsulfonyl or para-alkyl phenyl sulfonyl, preferably a paraalkylphenyl sulfonyl, anhydride or chloride having 7 to about 9 carbon atoms, i.e., the alkyl substituent is of 1 to about 3 carbon atoms, methanesulfonyl chloride or para-bromophenylsulfonyl chloride. Preferably, para-toluenesulfonyl chloride is employed. The reaction is slightly exothermic, and preferably, due to thermal instability of tosylates, the reaction is conducted under reduced temperatures, e.g., from about −5° to 10° C., preferably about 0° to 5° C. The sulfonic ester may be represented by the following structural formula:

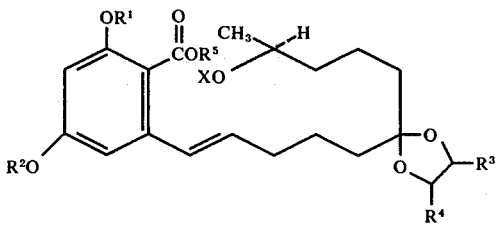

wherein R¹, R², R³, R⁴ and R⁵ are as defined above, and wherein X is CH₃

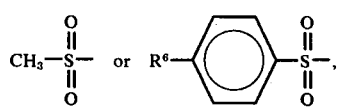

in which R⁶ is hydrogen, lower alkyl, e.g. of 1 to about 3 carbon atoms, preferably methyl, or bromine.

The sulfonic ester is then reacted with an amount in excess of that stoichiometrically required for complete reaction of tetraalkyl ammonium carboxylic ester of the formula

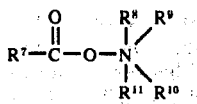

wherein $R^7$ is lower alkyl, preferably methyl, and $R^8$, $R^9$, $R^{10}$ and $R^{11}$ are also lower alkyl, but preferably ethyl. The reaction is conducted in an inert organic solvent such as methyl ethyl ketone, tetrahydrofuran, acetone, etc., under refluxing conditions, e.g., about 55° to 90° C. The reaction product, a carboxylic ester having the (R) structure, can be represented by the following structural formula:

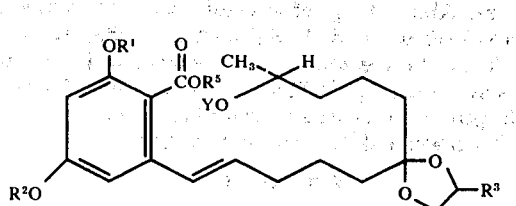

wherein $R^1$, $R^2$, $R^3$, $R^4$, and $R^5$ are as defined above and Y is

in which $R^7$ is as defined above. The inversion is accomplished without racemization to carboxylic esters of both the (R) and (S) structures.

In order to reform the lactone ring, the diester is hydrolyzed under strongly basic hydrolysis conditions to provide a hydroxy acid. Hydrolysis conditions include the presence of about 0.5 to 3 parts by weight of alkali metal hydroxide, e.g., sodium or potassium hydroxide, per part of the ester, a strong aprotic solvent such as dimethyl sulfoxide, dimethyl formamide, diethylene glycol dimethyl ether, and the like, and temperatures of about 90° to 140° C., preferably about 100° to 130° C. The hydrolyzed product, a resorcylic acid derivative, may be represented by the structural formula

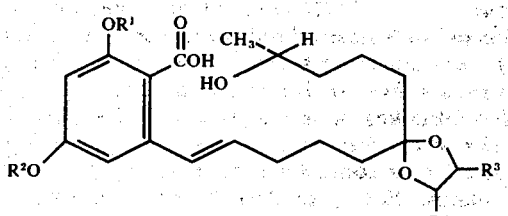

wherein $R^1$, $R^2$, $R^3$, and $R^4$ are as defined above. Under these hydrolysis conditions, the ketal moiety remains essentially unreacted.

The carbonyl function of the above-described resorcylic acid derivative may be regenerated by hydrolyzing the ketal group in the opened lactone ring in the presence of a catalytically-effective amount of a strong acid, for example, para-toluene sulfonic acid, hydrochloric acid, sulfuric acid, perchloric acid, and the like, in a medium containing aqueous tetrahydrofuran or other water soluble, organic solvent. The hydrolysis may be conducted at ambient temperatures, e.g., 10° to 35° C. The strong acid is employed in an amount of about 0.1 to 5, preferably about 0.5 to 2, parts by weight of acid per part of the resorcylic acid derivative. The structural formula of the product, a keto-substituted, resorcylic acid derivative may be represented as

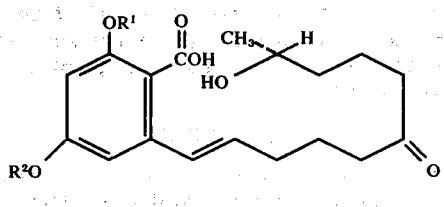

wherein $R^1$ and $R^2$ are as defined above. This conversion of the ketal group back to the keto group may, however, be effected subsequent to the re-forming of the lactone ring, discussed next.

The above-described keto-substituted acid derivative is then lactonized. The derivative may be lactonized by reacting it with trifluoroacetic anhydride in the presence of an organic solvent such a benzene, toluene, or the like. The trifluoroacetic anhydride is normally present in an amount in excess of that stoichiometrically required for the reaction. Desirably, the lactonization reaction is conducted under an inert atmosphere, e.g., a nitrogen atmosphere under the influence of cooling. The reaction temperature is normally maintained at about −5° to 10° C., preferably about 0° to 5° C. The resulting lactone has a structural formula which may be represented as

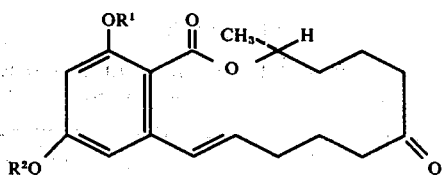

wherein $R^1$ and $R^2$ are as defined above. Another method of lactonizing the derivative is by the use of phosgene and triethylamine as is described by H. L. Wehrmeister and D. E. Robertson, Journal of Organic Chemistry, 33, page 4176 (1968), which is incorporated herein by reference.

Hydrogenolysis of the above-described lactone over a hydrogenation catalyst, for instance palladium on carbon, in the presence of an organic solvent under hydrogenation conditions yields (R)-zearalanone. The hydrogenolysis may be conducted at ambient conditions, e.g., 10° to 35° C., and atmospheric pressure.

The following examples are provided to further illustrate this invention.

EXAMPLE I (2-(10(S)-Hydroxy-6-oxo-trans-undecenyl)-4,6-dibenzyloxybenzoic Acid μ-Lactone)

Approximately 100 grams (g.) of (10'S)-zearalenone is dissolved in 500 milliliters (ml.) of dimethylsulfoxide, and 110 g. benzyl chloride and 160 g. of anhydrous potassium carbonate are added to the mixture. The mixture is heated for about seven hours on a steam bath and then cooled to room temperature. The cooled mixture is diluted with water and extracted with chloroform. The extract is washed several times with water and dried over sodium sulfate. After removal of the chloroform, 194 g. of residue are provided. Recrystallization of the residue twice from isopropyl alcohol provided 138 g. of white crystals of 2-(10(S)-hydroxy-6-oxo-trans-undecenyl)-4,6-dibenzyloxybenzoic acid μ-lactone. The crystals have a melting point of about 128.5° to 129.5° C.

EXAMPLE II (2-(10(S)-Hydroxy-6-ethylenedioxy-trans-undecenyl)-4,6-dibenzyloxybenzoic Acid μ-Lactone)

2-(10(S)-Hydroxy-6-oxo-trans-undecenyl-4,6-dibenzyloxybenzoic acid μ-lactone in the amount of 200 g. of admixed with 400 ml. of ethylene glycol, 2 g. of para-toluenesulfonic acid, and 3.5 l. of toluene. The mixture is slowly distilled to remove water which is formed in the reaction. The mixture is periodically subjected to a Zimmerman test to determine the presence of alpha-methylene ketones. A negative test result is obtained after 45 hours. The mixture is then cooled and diluted with diethyl ether and washed successively with water, a 5 percent aqueous sodium hydroxide solution, water, and a saturated aqueous sodium chloride solution. The solids are dried over sodium sulfate, and the solvents removed to provide 218 g. of residue. The residue is further purified by chromatography on one kg. of Florisil, a powdered magnesia-silica gel absorbent, using a two percent methanol in benzene solvent. A colorless glass of 213 g. of 2-(10(S)-hydroxy-6-ethylenedioxy-trans-undecenyl)-4,6-dibenzyloxybenzoic acid μ-lactone is obtained.

EXAMPLE III (2-(10(S)-Hydroxy-6-ethylenedioxy-trans-undecenyl)-4,6-dibenzyloxybenzoic Acid)

To a solution of 37 g. of 2-(10(S)-hydroxy-6-ethylenedioxy-trans-undecenyl)-4,6-dibenzyloxybenzoic acid μ-lactone in 400 ml. dimethylsulfoxide is added 100 ml. of an aqueous 40 percent sodium hydroxide solution. This mixture is heated for 5 hours at 120° C. under an inert atmosphere of nitrogen. The resulting red solution is cooled, poured over ice, acidified with an aqueous 10 percent solution of sulfuric acid, and extracted with chloroform. The extract is washed several times with water and dried over sodium sulfate. Upon removal of the solvents, 31 g. of cream colored solid is obtained. The cream colored solid is recrystalized from a hexane-benzene solvent to provide 25 g. of 2-(10(S)-hydroxy-6-ethylenedioxy-trans-undecenyl)-4,6-dibenzyloxybenzoic acid as an amorphous, white solid melting at about 104° to 106° C. This solid analyzes as containing 73.04 weight percent carbon and 7.42 weight percent hydrogen, as compared to theoretical values of 72.83% carbon and 7.19% hydrogen.

EXAMPLE IV (Methyl 2-(10(S)-hydroxy-6-ethylenedioxy-transundecenyl)-4,6-dibenzyloxybenzoate)

To a suspension of 48 g. of 2-(10(S)-hydroxy-6-ethylenedioxy-trans-undecenyl)-4,6-dibenzyloxybenzoic acid in 300 ml. of benzene is added a stoichiometric excess of diazomethane in 250 ml. of diethyl ether. The diazomethane is freshly prepared from N-methylnitrosourea. The solution becomes light yellow and is stirred for 15 minutes after the addition of the diazomethane. Acetic acid is then added to the mixture to decompose the excess diazomethane, and the solvents are removed to provide 48.8 g. of light yellow oil. The oil is purified by chromatography on 1250 g. of SilicAR, CC-7, an absorbent silica gel obtainable from Mallinckrodt Chemical Works, using a chloroform solvent. About 41 g. of a colorless oil of methyl 2-(10(S)-hydroxy-6-ethylenedioxy-trans-undecenyl)-4,6-dibenzyloxybenzoate are obtained. This oil analyzes as containing 72.92 wt. % carbon and 7.24 wt. % hydrogen, as compared to theoretical values of 73.17 wt. % carbon and 7.32 wt. % hydrogen.

EXAMPLE V (Methyl 2-(10(S)-tosyl-6-ethylenedioxy-trans-undecenyl)-4,6-dibenzyloxybenzoate)

A solution of 32 g. of methyl 2-(10(S)-hydroxy-6-ethylenedioxy-trans-undecenyl)-4,6-dibenzyloxybenzoate in 400 ml. of anhydrous pyridine is cooled in an ice bath to 5° C. To the cooled mixture is added 12.4 g. of freshly recrystallized para-toluenesulfonyl chloride in several portions. The reaction mixture is maintained at 5° C. under continuous stirring. After 44 hours, the mixture is diluted with water and extracted with chloroform. The extract is washed successively with water, an aqueous solution of 5 percent hydrochloric acid and an aqueous solution of 5 percent sodium bicarbonate, then dried over sodium sulfate and potassium carbonate. Removal of the chloroform on a rotary evaporator at room temperature under vacuum provided 36 g. of crude methyl 2-(10(S)-tosyl-6-ethylenedioxy-trans-undecenyl-4,6-dibenzyloxybenzoate.

EXAMPLE VI (Methyl 2-(10(R)-acetoxy-6-ethylenedioxy-trans-undecenyl)-4,6-dibenzyloxybenzoate)

In 700 ml. of methyl ethyl ketone is dissolved 36 g. of methyl 2-(10(S)-tosyl-6-ethylenedioxy-trans-undecenyl)-4,6-dibenzyloxybenzoate and 36 g. of tetraethyl ammonium acetate tetrahydrate. The mixture is refluxed for about 46 hours, and then cooled and the methyl ethyl ketone is removed. The mixture is dissolved in chloroform, washed several times with water, and dried over sodium sulfate. Upon removal of the chloroform, 26.1 g. of dark brown oil is obtained. Chromatography on 1 kg. of SilicAR, CC-7, using a chloroform solvent, provides 10.2 g. of methyl 2-(10(R)-acetoxy-6-ethylenedioxy-trans-undecenyl)-4,6-dibenzyloxybenzoate which analyzes as containing 72.11 wt. % carbon and 7.03 wt. % hydrogen, as compared with theoretical values of 72.08 % carbon and 7.14 % hydrogen. The remaining chromatography fractions contain olefinic and hydroxylic material which are the result of an elimination side reaction and a substitution with water side reaction, respectively.

EXAMPLE VII (2-(10(R)-Hydroxy-6-ethylenedioxy-trans-undecenyl)-4,6-dibenzyloxybenzoic Acid)

A solution of 38 g. methyl 2-(10(R)-acetoxy-6-ethylenedioxy-trans-undecenyl)-4,6-dibenzyloxybenzoate in 400 ml. of dimethylsulfoxide is heated to 120° C. To the heated mixture is added 100 ml. of an aqueous 40% sodium hydroxide solution under a nitrogen atmosphere. The mixture is heated at 120° C. for 5 hours, cooled to room temperature, and diluted with water. The diluted mixture is washed two times with diethyl ether and acidified with an aqueous solution of 30 percent sulfuric acid, and extracted with chloroform. The chloroform extract is washed with water and a saturated aqueous solution of sodium chloride and dried over sodium sulfate. After removal of the chloroform, 36 g. of brown oil is obtained which is partially purified by dissolving it in a methanol solvent and treating it with charcoal. Upon concentration of the treated mixture, a light yellow residue is provided. Recrystallization of the residue from a hexane and benzene solution provides 21 g. of 2-(10(R)-hydroxy-6-ethylenedioxy-trans-undecenyl)-4,6-dibenzyloxybenzoic acid having a melting point of about 104° to 106° C. This solid analyzes as containing 72.6 wt. % carbon and 7.42 wt. % hydrogen as compared with theoretical values of 72.83 % carbon and 7.19 % hydrogen.

EXAMPLE VIII (2-(10(R)-Hydroxy-6-oxo-trans-undecenyl)-4,6-dibenzyloxybenzoic Acid)

To a solution of 20 g. of 2-(10(R)-hydroxy-6-ethylenedioxy-trans-undecenyl)-4,6-dibenzyloxybenzoic acid in 150 ml. of tetrahydrofuran is added, while cooling, 100 ml. of an aqueous solution containing 220 g. perchloric acid per liter. The mixture is stirred for 6 hours at room temperature, then poured into water and extracted with chloroform. The extract is washed with water and an aqueous solution saturated with sodium chloride and is dried over sodium sulfate. Upon removal of the solvents, 17.8 g. of oil containing 2-(10(R)-hydroxy-6-oxo-trans-undecenyl)-4,6-dibenzyloxybenzoic acid are obtained.

EXAMPLE IX (2-(10(R)-Hydroxy-6-oxo-trans-undecenyl)-4,6-dibenzyloxybenzoic Acid $\mu$-Lactone)

To a solution of 10 g. 2-(10(R)-hydroxy-6-oxo-trans-undecenyl)-4,6-dibenzyloxybenzoic acid in 2.5 l. of anhydrous benzene which is cooled to 5° C in an ice bath is slowly added 4.2 g. of trifluoroacetic acid anhydride over a thirty minute period under a nitrogen atmosphere. The mixture is maintained at 5° C. under stirring for 24 hours. The reaction mixture is washed successively with an aqueous solution of 5 percent potassium hydroxide, water, a saturated aqueous solution of sodium chloride, and dried over sodium sulfate. Upon removal of the benzene, 6.3 g. of brown residue is obtained which is subjected to recrystallization from isopropyl alcohol several times to provide 1.8 g. of 2-(10(R) -hydroxy-6-oxo-trans-undecenyl)-4,6-dibenzyloxybenzoic acid $\mu$-lactone as white crystals melting at about 128.5° to 129.5° C. These crystals analyze as containing 77.08 wt. % carbon and 7.18 wt. % hydrogen, as compared with theoretical values of 77.11 % carbon and 6.83 % hydrogen.

EXAMPLE X ((10'R)-Zearalanone)

A solution of 1 g. of 2-(10(R)-hydroxy-6-oxo-trans-undecenyl)-4,6-dibenzyloxybenzoic acid-$\mu$-lactone in 140 ml. of a solvent containing 2.5 parts ethanol to 1 part ethyl acetate is hydrogenated over 0.3 g. of 5 percent palladium on carbon hydrogenation catalyst at atmospheric pressure and room temperature. Filtration of the catalyst and removal of the solvents provides 0.60 g. of white solid which is then recrystallized from methanol to obtain essentially pure, white crystals of (10'R)-zearalanone having a melting point of 190°–191° C. and a specific rotation at 25° C. using sodium light, of +36.8°.

Uterotropic assays are conducted on pure (10'R)-zearalanone, pure (10'S)-zearalanone, and a 50/50 mixture of (10'R)- and (10'S)-zearalanone. Each assay is conducted by orally administering to groups of ten, adult, castrate, female mice the test compound in sesame oil for three days at dosage levels of 50, 100, and 300 $\mu$g of the test compound per mouse per day. On day four the animals are sacrificed and the uteri are removed and weighed. The results are as follows:

| Test Compound | Total Dose ($\mu$g) | Final Body Weight (g) | Uterine Weight (mg) | % Body Weight |
|---|---|---|---|---|
| Control | — | 26.1 | 11.3 | 0.043 |
| (10'R)-Zearalanone | 150 | 26.5 | 9.8 | 0.037 |
|  | 300 | 26.4 | 11.6 | 0.044 |
|  | 900 | 26.5 | 9.6 | 0.036 |
| (10'S)-Zearalanone | 150 | 26.2 | 28.1 | 0.107 |
|  | 300 | 26.0 | 34.5 | 0.133 |
|  | 900 | 27.2 | 50.7 | 0.187 |
| (10'R,S)-Zearalanone (1:1 mixture) | 150 | 23.5 | 25.5 | 0.108 |
|  | 300 | 22.9 | 34.3 | 0.149 |
|  | 900 | 24.0 | 53.6 | 0.223 |

The above data illustrate the uterotropic activity enhancing effect that (10'R)-zearalanone has on (10'S)-zearalanone. Whereas (10'R)-zearalanone when used alone fails to stimulate uterine growth, when it is used as an additive to (10'S)-zearalanone the latter stimulates uterine growth about twice as much as does unaugmented (10'S)-zearalanone.

It is claimed:

1. A method of preparing (10'R)-zearalanone from (10'S)-zearalenone comprising:
  protecting the phenolic hydroxy and carbonyl groups of (10'S)-zearalenone;
  cleaving the lactone linkage in the protected (10'S)-zearalenone in an alkaline medium to provide a hydroxy acid;
  esterifying the hydroxy acid to provide a hydroxy ester;
  treating the hydroxy ester with methane sulfonyl chloride or an anhydride or chloride of a phenyl sulfonyl of the formula

wherein R¹ is hydrogen, lower alkyl, or bromine to provide a sulfonic ester;

inverting the structure of the sulfonic ester from (S) to (R) by reacting the sulfonic ester with a tetraalkylammonium carboxylic ester of the formula

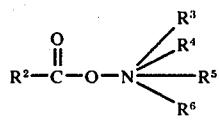

wherein each of R², R³, R⁴, R⁵ and R⁶ is lower alkyl, and thereby providing a carboxylic ester;

hydrolyzing the carboxylic ester in an alkaline medium to provide a hydroxy acid having the inverted structure;

lactonizing the hydroxy acid having the inverted structure; and hydrogenolyzing the lactone in the presence of a catalytically effective amount of hydrogenation catalyst to provide (10'R)-zearalanone.

2. The method of claim 1 wherein the hydroxy ester is reacted with para-toluene sulfonyl chloride to provide the sulfonic ester.

3. The method of claim 1 wherein the sulfonic ester is reacted with tetraethyl ammonium acetate to provide the carboxylic ester.

4. The method of claim 1 wherein the hydrogenation catalyst is palladium on carbon.

5. A method of preparing (10'R)-zearalanone from (10'S)-zearalenone comprising condensing the phenolic functions and ketalyzing the carbonyl function of the (10'S)-zearalenone to provide (A) a compound of the formula

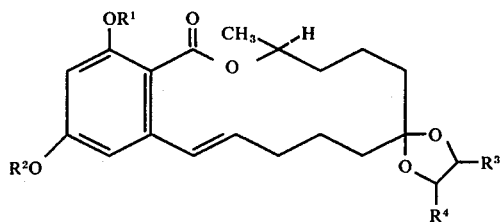

A in which R¹ and R² are carbon containing, cyclic substituents of 5 to 12 ring members or lower alkoxyalkyl, and R³ and R⁴ are hydrogen or lower alkyl wherein said condensation is effected by reaction with a corresponding chloride of R¹ and R² and said ketalizaton is effected by reaction with a diol of the formula R³CH(OH)CH(OH)R⁴;

cleaving the lactone linkage of (A) in an alkaline medium to provide (B) a compound of the formula

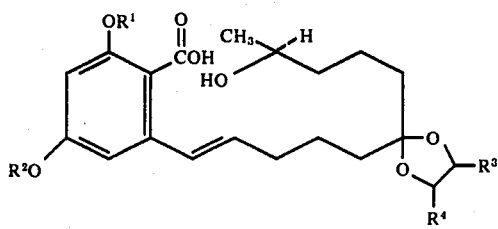

B esterifying the carboxyl function of (B) with diazomethane to provide (C) a compound of the formula

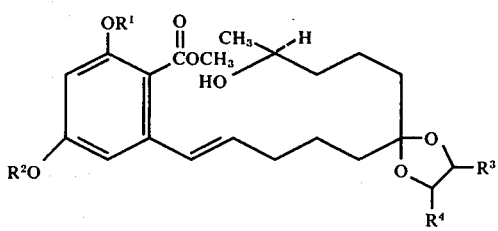

C treating (C) with methane sulfonyl chloride, para-bromophenyl sulfonyl chloride, phenyl sulfonyl chloride, phenyl sulfonyl anhydride, alkyl phenyl sulfonyl anhydride or chloride having 7 to about 9 carbon atoms to provide (D) a compound of the formula

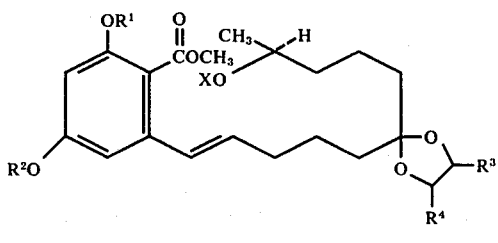

D wherein X is

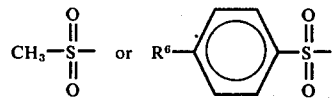

in which R⁶ is bromine, hydrogen, alkyl of 1 to 3 carbon atoms;

inverting the structure of (D) from (S) to (R) by reacting (D) with a tetraalkyl ammonium carboxylic ester of the formula

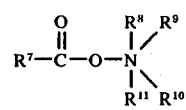

wherein each of R⁷, R⁸, R⁹, R¹⁰, and R¹¹ is lower alkyl, to provide (E) a compound of the formula

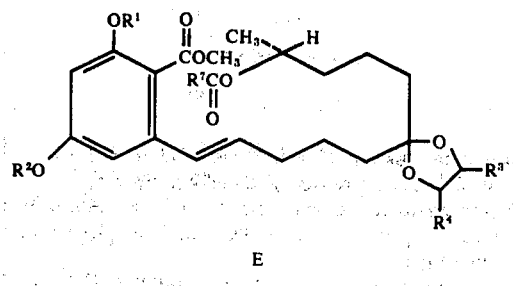

E hydrolyzing (E) in a strong alkaline medium and regenerating the carboxyl function by hydrolysis with a strong acid to provide (F) a compound of the formula

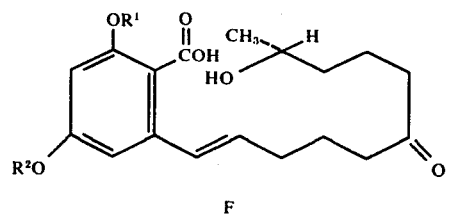

F lactonizing (F) with trifluoroacetic acid anhydride to provide (G) a compound of the formula

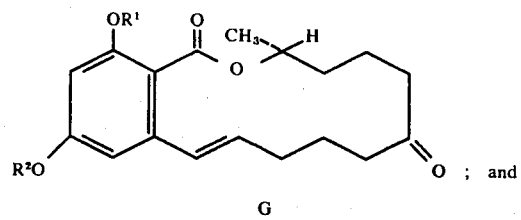

G ; and hydrogenolyzing (G) in the presence of a catalytically-effective amount of hydrogenation catalyst to provide (10'R)-zearalanone.

6. The method of claim 5 wherein the condensation of the phenolic functions of (10'S)-zearalenone is conducted with benzyl chloride, the ketalization is conducted with ethylene glycol, para-toluene sulfonyl chloride is employed to treat (C), and the structure of (D) is inverted using tetraethyl ammonium acetate.

7. The method of claim 6 wherein (D) is refluxed with tetraethyl ammonium acetate in the presence of an inert organic solvent.

8. The method of claim 5 wherein (A) is cleaved in a strong alkaline medium to provide (B).

9. A method of inverting (I) a compound of the formula

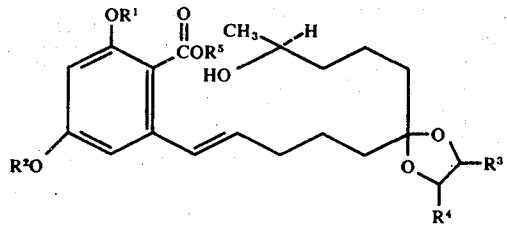

I wherein $R^1$ and $R^2$ are carbon-containing, cyclic substituents of 5 to 12 members; $R^3$ and $R^4$ are hydrogen or lower alkyl; and $R^5$ is lower alkyl; to (II) a compound of the formula

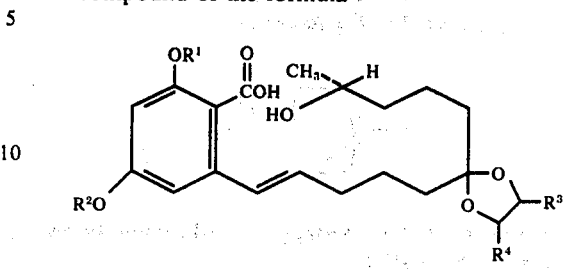

II comprising:
treating (I) with methane sulfonyl chloride, para-bromophenyl sulfonyl chloride, or phenyl-sulfonyl or a para-alkyl phenyl sulfonyl anhydride or chloride having 7 to about 9 carbon atoms to provide (III) a compound of the formula

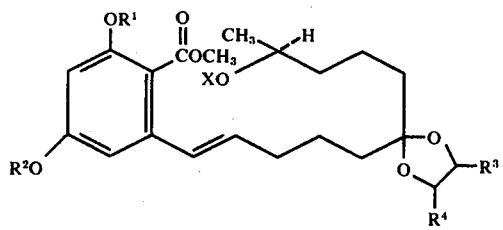

III wherein X is

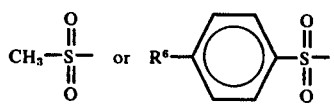

in which $R^6$ is bromine, hydrogen, or alkyl of 1 to 3 carbon atoms;

reacting (III) with a tetraalkyl ammonium carboxylic ester of the formula

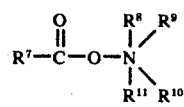

wherein each of $R^7$, $R^8$, $R^9$, $R^{10}$ and $R^{11}$ is lower alkyl to provide (IV) a compound of the formula

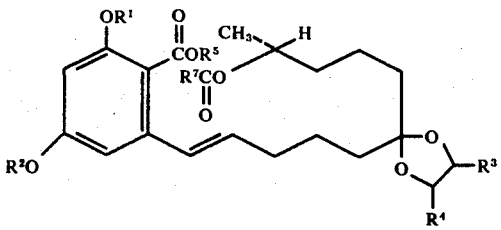

IV hydrolyzing (IV) in a strongly alkaline medium in the presence of an aprotic solvent to provide (II).

10. A method of preparing (10'R)-zearalanone from (10'S)-zearalenone comprising:
treating a hydroxy ester of zearalenone with methane sulfonyl chloride or an anhydride or chloride of a phenyl sulfonyl of the formula

where R¹ is hydrogen, lower alkyl, or bromine to provide a sulfonic ester;
inverting the structure of the sulfonic ester from (S) to (R) by reacting the sulfonic ester with a tetraalkylammonium carboxylic ester of the formula

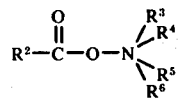

wherein each of $R^2$, $R^3$, $R^4$, $R^5$ and $R^6$ is lower alkyl, and thereby providing a carboxylic ester;
hydrolyzing the carboxylic ester in an alkaline medium to provide a hydroxy acid having the inverted structure;
lactonizing the hydroxy acid having the inverted structure; and
hydrogenolyzing the lactone in the presence of a catalytically effective amount of hydrogenation catalyst to provide (10'R)-zearalanone.

* * * * *